United States Patent
Rupprecht et al.

(10) Patent No.: US 6,308,705 B1
(45) Date of Patent: Oct. 30, 2001

(54) INTEGRATED LUNG THERAPY METHOD

(75) Inventors: Thomas Rupprecht, Uttenreuth; Rainer Kuth, Herzogenaurach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/467,881

(22) Filed: Dec. 21, 1999

(51) Int. Cl.$^7$ .................................................. A61M 16/00
(52) U.S. Cl. ..................... 128/204.18; 424/9.3; 600/529; 600/530; 600/531; 600/532; 600/533; 600/534; 600/535; 600/536; 600/537; 600/538; 600/539; 600/540; 600/541; 600/542; 600/543
(58) Field of Search .............. 128/204.18; 600/529–543; 424/9.3

(56) References Cited

U.S. PATENT DOCUMENTS 5,215,680 * 6/1993 D'Arrigo ............................. 252/307
5,985,309 * 11/1999 Edwards et al. ..................... 424/426
6,042,809 * 3/2000 Tournier et al. ..................... 424/9.3

* cited by examiner

Primary Examiner—John G. Weiss
Assistant Examiner—Darwin Erezo
(74) Attorney, Agent, or Firm—Schiff Hardin & Waite

(57) ABSTRACT

In a lung therapy method, hyperpolarized gas is administered for one breath to a subject, and a magnetic resonance scan of at least one lung of the subject is conducted. The data obtained from the scan are evaluated, specifically to determine the extent and distribution of infusion of hyperpolarized gas in the lung, as an indication of the alveolae in the lung which are open. Based on the evaluation of the data obtained in the magnetic resonance scan, a determination is made as to whether administration of a surfactant is necessary in order to improve opening of the lung. If a surfactant is administered, the procedure can be repeated to obtain an updated dataset, which can be evaluated to determine whether the administered surfactant has been effective.

6 Claims, 1 Drawing Sheet

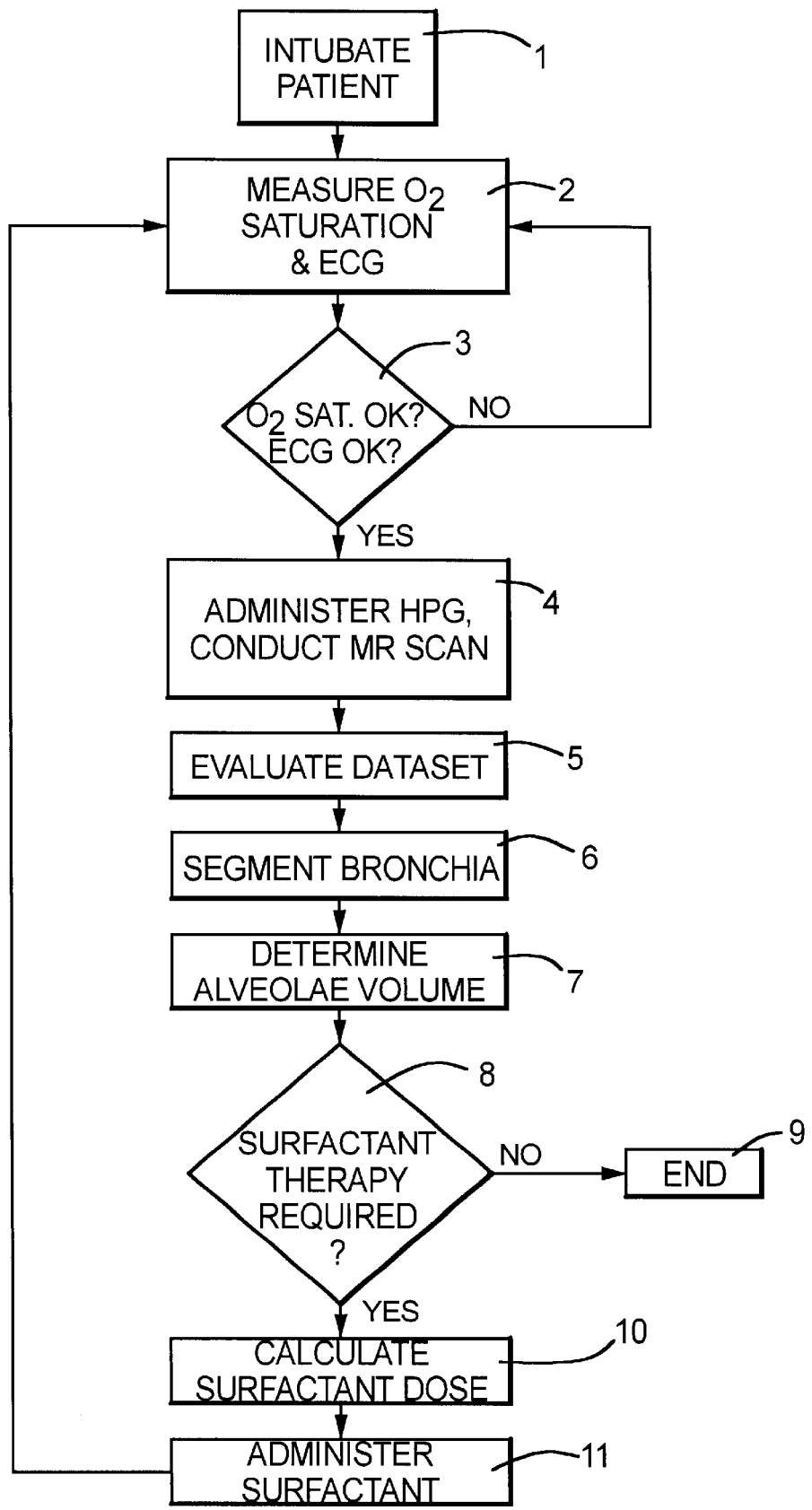

INTEGRATED LUNG THERAPY METHOD

BACKGROUND OF THE INVENTION

1. Field of the Invention

The present invention is directed to a method for lung therapy, and in particular to a method for lung therapy employing magnetic resonance (MR) imaging.

2. Description of the Prior Art

The pulmonary alveolae in healthy persons are maintained in shape by a film of surfactant, which is a complex mixtures of sphingolipids and proteins, so that the alveolae are uniformly filled with air when the person inhales. Under certain circumstances, for example, as a result of an infection, or immaturity of the lung, or circulatory damage, a degradation of this surfactant film occurs, and the pulmonary alveolae collapse and are no longer filled with fresh air. An exchange of $O_2$ and $CO_2$ then can no longer ensue between the inhaled air and the blood. This problem also frequently arises with premature babies, because premature babies have not yet built up enough surfactant. As a treatment for this phenomenon, a medication selected from various types of artificial surfactant preparations is administered to the patient in the respiratory path. This serves as a substitute for the surfactant which is present in a healthy person. In administering this surfactant, however, it is very difficult to select and maintain an appropriate dose.

The extent to which a lung has collapsed, and the spatial distribution of the collapsed portion of the lung, are not known before administering the medication therapy. After administration of the surfactant, it is uncertain where, within the lung, the administered surfactant has taken effect. Conventional imaging techniques do not supply information which adequately spatially resolved to allow such a determination to be made. An overdose of surfactant can lead to complications such as deficient aeration, due to the excess quantity of medication presenting a physical disturbance to breathing. An inadequate dose produces an insufficient effect to address the pathology. An optimum form of surfactant administration, such as administration in solvents, aerosol, etc., has not yet been found. Other more radical therapies, such as surgical removal of a passive portion of a lung, likewise require functional information so that healthy tissue is not excised.

SUMMARY OF THE INVENTION

An object of the present invention is to provide a technique for lung therapy which allows a relatively precise determination of a collapsed portion of a lung to be identified, so that an appropriate medication dosage can be selected.

It is a further object of the present invention to provide a lung therapy technique which allows the effect of a medication, administered to a person having a collapsed or partially collapsed lung, to be monitored.

The above object is achieved in accordance with the principles of the present invention in a method for integrated lung therapy wherein the patient is artificially ventilated and the residual volume of the lung of the patient is determined before the administration of a surfactant. The patient is then ventilated with a hyperpolarized gas for one breath, instead of being ventilated with air or an air/$O_2$ mixture. A high resolution magnetic resonance image of the now-ventilated portion of the lung is then obtained. Alternatively, a series of images of the time curve of the dispersion of the HPG within the lung can be obtained, or a number of successive tomograms of the lung can be obtained. In these images, alveolae which are open, and thus contain the HPG, can be clearly differentiated from collapsed alveolae, which contain little or no HPG. The need for administration of a surfactant, and the optimum form of administration, can then be determined on the basis of these images.

The administration of the surfactant, for example, can be determined by automatically or semi-automatically segmenting the bronchia in the two-dimensional or three-dimensional dataset represented in the image or images, and the components representing the gas quantities in the bronchia and alveolae can be integrated on the basis of signal density and distribution. After a waiting time of typically one minute, and when adequate oxygen saturation in the blood exists, HPG is again administered to the patient, and another MR scanning takes place. The images acquired in this subsequent scan are compared to the previous series, and the therapy is modified, continued or ended as warranted.

DESCRIPTION OF THE DRAWING

The single FIGURE is a flowchart of an integrated lung therapy method in accordance with the principles of the present invention.

DESCRIPTION OF THE PREFERRED EMBODIMENTS

As set forth in the flowchart in the FIGURE, a patient who may need administration of a surfactant in order to treat a collapsed or partially collapsed lung, is connected to a ventilator, such as by intubating the patient, in step 1. Normally, the ventilator supplies the patient with air or an air/$O_2$ mixture in a conventional manner. In order to obtain baseline data, in the course of this conventional ventilation, $O_2$ saturation is measured and an ECG is obtained in step 2. A determination is then made in step 3 as to whether the $O_2$ saturation and the ECG are satisfactory, so that the baseline data can be considered as being reliable. If not, adjustments or corrections dictated by the attending physician are made, and step 2 is repeated, and another check is made, until it is determined that the $O_2$ saturation and the ECG are satisfactory.

When this point is reached, hyperpolarized gas (HPG) is administered to the patient in step 4, and a magnetic resonance scan of the subject is conducted using an image sequence to produce data or images wherein tissue infused with the HPG is made easily distinguishable from surrounding tissue which is not infused with HPG. In general terms, the use of HPG in the context of magnetic resonance scanning is well-known to those of ordinary skill in the art, and suitable scanning sequences are therefore also well-known.

The dataset, representing one or more images, obtained from the magnetic resonance scan is then evaluated in step 5. This evaluation can encompass the display and evaluation of one of more magnetic resonance images. The evaluation of the dataset in step 5, however, can also or alternatively include statistical evaluation of the data contained within the dataset. For example, as set forth in step 6, the bronchia can be automatically or semiautomatically segmented in the dataset (which may be a two-dimensional dataset or a three-dimensional dataset) and the gas quantities in the bronchia and alveolae can be integrated on the basis of signal density and distribution. from the evaluation, the total volume of open alveolae is then determined in step 7.

Based on this information, the physician can then make a determination in step 8 as to whether surfactant therapy is required. If the physician determines that no surfactant therapy is required, the method ends at step 9.

If surfactant therapy is required, in step 10 the same information used to determine whether surfactant therapy is required, or information derived therefrom, is used to calculate an appropriate surfactant dose in step 10. The calculated surfactant dose is then administered in step 11.

After a brief waiting time, such as approximately one minute, at least steps 2 through 8 are repeated. The data obtained from the repeated scan are compared to the data obtained from the original scan, so that the effectiveness of the administered surfactant can be determined. Based on this comparison, the physician in step 8 of the repeated method makes a determination as to whether to again repeat the process with another surfactant dose and, if so, whether the same surfactant dose should be used as was previously administered, or whether a modified dose should be used. Of course, the physician may also be satisfied with the results after the repeated scan, and may determine that the procedure should end at step 9 at that point.

Although modifications and changes may be suggested by those skilled in the art, it is the intention of the inventors to embody within the patent warranted hereon all changes and modifications as reasonably and properly come within the scope of their contribution to the art.

We claim as our invention:

1. A lung therapy method comprising the steps of:

ventilating a patient with respiratory gas;

administering hyperpolarized gas to said patient during one respiratory cycle;

conducting a magnetic resonance scan of a lung of the subject after administering the hyperpolarized gas to obtain a dataset representing infusion of the hyperpolarized gas in said lung;

evaluating said dataset to determine a volume of open alveolae in said lung;

dependent at least on said volume of open alveolae, determining whether administration of a surfactant to said subject is required and, if so, calculating a surfactant dose and administering said surfactant dose to said subject.

2. A method as claimed in claim 1 comprising obtaining a two-dimensional dataset from said magnetic resonance scan.

3. A method as claimed in claim 1 comprising obtaining a three-dimensional dataset from said MR scan.

4. A method as claimed in claim 1 comprising, for evaluating said dataset, segmenting bronchia in said lung and determining said volume of open alveolae by integrating signal density and distribution of signals in said dataset arising from said hyperpolarized gas.

5. A method as claimed in claim 1 comprising the additional steps of:

after administering said surfactant dose, a waiting a time and again administering hyperpolarized gas to said subject;

after again administering said hyperpolarized gas to said subject, conducting another magnetic resonance scan of said subject to obtain an updated dataset;

determining an updated volume of open alveolae in said lung from said updated dataset; and determining whether further administration of a surfactant dose is necessary by comparing said volume of open alveolae to said updated volume of open alveolae.

6. A method as claimed in claim 5 wherein said time comprises approximately one minute.

* * * * *